United States Patent
Handa et al.

(10) Patent No.: US 6,949,586 B2
(45) Date of Patent: Sep. 27, 2005

(54) SYNERGISTIC COMPOSITION OF TRANS-TETRACOS-15-ENOIC ACID AND APOCYNIN AND METHOD OF TREATMENT FOR HEPATOTOXICITY

(75) Inventors: Sukhdev Swami Handa, Jammu (IN); Om Parkash Suri, Jammu (IN); Vishwa Nath Gupta, Jammu (IN); Krishan Avtar Suri, Jammu (IN); Naresh Kumar Satti, Jammu (IN); Vikram Bhardwaj, Jammu (IN); Bupinder Singh, Jammu (IN); Bal Krishan Chandan, Jammu (IN)

(73) Assignee: Council of Scientific Research (IN)

( * ) Notice: Subject to any disclaimer, the term of this patent is extended or adjusted under 35 U.S.C. 154(b) by 144 days.

(21) Appl. No.: 10/102,147

(22) Filed: Mar. 20, 2002

(65) Prior Publication Data

US 2003/0157198 A1 Aug. 21, 2003

Related U.S. Application Data

(63) Continuation-in-part of application No. 10/073,548, filed on Feb. 11, 2002.

(51) Int. Cl.$^7$ ............ A61P 1/16; A61K 35/78; A61K 31/19; A61K 31/12; A61K 35/00
(52) U.S. Cl. .......... 514/560; 424/725; 514/689; 514/699; 514/717
(58) Field of Search .......... 424/725; 514/560, 514/689, 699, 717

(56) References Cited

U.S. PATENT DOCUMENTS

| | | | | |
|---|---|---|---|---|
| 5,194,448 A | * | 3/1993 | Coupland et al. | 514/558 |
| 5,763,496 A | * | 6/1998 | Holland | 514/689 |
| 5,994,404 A | * | 11/1999 | Coupland | 514/560 |
| 6,090,851 A | * | 7/2000 | Dodd-o | 514/689 |
| 6,492,429 B1 | * | 12/2002 | Graus et al. | 424/725 |
| 6,495,170 B1 | * | 12/2002 | Smit et al. | 424/725 |

OTHER PUBLICATIONS

Ansari, et al., "Hepatoprotective activity of kutkin—the iridoid glycoside mixture of Picrorhiza kurrooa", Indian Journal Med. Res., Aprl. pp. 404–404 (1988).

Dey, A.C., "Indian Medicinal Plants used in Ayurvedic Preparations", Bishen Singh Mahendra Pal Singh, pp. 81–82, (1980).

Finnemore, H., "The Constituents of Canadian Hemp. Part I. Apocynin", J. Chem. Soc., vol. XCIII, pp. 1513–1520 (1908).

Handa, et al., "Natural Prducts and Plants as Liver Protecting Drugs", FITOTERAPIA, vol. LVII, No. 5, pp. 307–351 (1986).

Jayaweera, D.M.A., "Medicinal Plants (Inigenous and Exotic) Used in Ceylon", The National Science Council of Sri Lanka, Colombo, Part V, p. 76(1982).

Langar, J.G., "Clinical trials on Picrorhiza kurroa as an immunoregulator", Indian Journal of Pharmacology, vol. 13, No. 1, pp. 98–99, Jan.–Mar. (1981).

Nadkarni, K.M., Indian Materia Medic, vol. 1, Popular Book Depot, Bombay, pp. 25–27; 619–622; 634–651; 953–955; 1220–1221, 1252–1253, (1954).

Suri, O.P., "Synthesis of Apocynin, a Choleretic Constituent of Picrorhiza kurroa & Its Homologues", Indian Journal of Chemistry, vol. 26B, No. 6, pp. 587–588, Jun. (1987).

* cited by examiner

*Primary Examiner*—Herbert J. Lilling
(74) *Attorney, Agent, or Firm*—Fish & Richardson, P.C.

(57) ABSTRACT

The present invention relates to a synergistic hepatoprotective pharmaceutical composition comprising an effective amount of trans-tetracos-15-enoic acid (TCA) and Apocynin (APO), the present invention also relates to a method of treatment for hepatotoxicity in mammals and humans.

36 Claims, No Drawings

SYNERGISTIC COMPOSITION OF TRANS-TETRACOS-15-ENOIC ACID AND APOCYNIN AND METHOD OF TREATMENT FOR HEPATOTOXICITY

This is a Continuation Application of U.S. patent application Ser. No. 10/073,548, filed on Feb. 11, 2002 titled as "A pharmaceutical composition and process for isolation of trans-tetracos-15-enoic acid and method of treatment of hepatotoxicity".

FIELD OF INVENTION

The present invention relates to a synergistic hepatoprotective composition comprising trans-tetracos-15-enoic acid (TCA) and Apocynin (APO). The present invention also relates to a method of treatment of hepatotoxicity in mammals and humans.

BACKGROUND AND PRIOR ART REFERENCES

Apocynin, a cardiotonic constituent of the rhizomes of *Apocyanum cannabium* [Finnemore Horace, J. Chem. Soc. 93 (1908) 1513–1520] and *A. androsaemifolium* [Naves Yves-Rene, Helv Chim Acta 32 (1949) 1351] and essential oils of the rhizomes of Iris species have been reported to be responsible for choleretic activity of *Picrorhiza kurroa* [Basu, K., Dasgupta B., Bhattacharya, S. K. and Debnath, P. K. Curr Sci, 40 (1971) 603]. The constituent has been synthesized and pharmacologically evaluated [Suri, O. P., Bindra, R. S., Satti, N. K. and Khajuria, R. K. Indian Journal of Chemistry, 26B (1987), p 587–88]. Apocynin has also been evaluated for antioxidant and free radical scavenging activities.

Roots of *Picrorhiza kurroa* are used therapeutically in traditional medicine of almost all Asian countries to treat a manifold of conditions of illness including liver, lung & spleen ailments [Rajaram, D. (1976) Bomb. Hosp. Journal, 18, 66–69; Pandey, G. S. (1979) Indian Materia Medica, Chaukhamba Sanskrit Sausthan, Varanasi pp 70–71; Langar, J. G., Gupta, O. P. and Atal, C. K. (1981), Ind. J. Pharm. 13, 98–99; Handa, S. S., Sharma, A. and Chakraborty, K. K. (1986), Fitotherapia, 58, 307–351; Ansari, R. R., Kapoor, N. K., Kulshreshta, D. K., Mehta, H., Mehrotra, B. N., Patnaik, G. K. and Sharma, S. K. (1988), Indian J. Med. Plants, 87, 401–404] and inflammatory disorders [Nadkarni, K. M. (1954), Indian Materia Medica, vol. 1, Popular Book Depot, Bombay pp. 25–27, 619–622, 634–651, 953–955, 1220–1221, 1252–53; Dey, A. C. (1981), Indian Medicinal Plants used in Ayurvedic Preparations, Bishan Singh & Mahendra Pal Singh, Dehra Dun, India pp 81–82; Jayaweera, D. M. A. (1982) Medicinal Plants used in Ceylon, The National Science Council of Sri Lanka, Colombo, Sri Lanka, part 5, pp 76]. Hepatoprotective, Immunostimulant & Immunorestorative formulations based on P. Kurroa chemical constituents, mainly iridoid glycosides, have been developed at CDRI Lucknow & RRL Jammu [450/ DEL/89 & 845/ DEL/92].

Literature survey revealed that earlier reports showed the presence of trans-tetracos-15-enoic acid in Jojoba oil ex. *Simmondsia chinensis* seeds (0.62–1.11%) and cis isomer of the acid is reported in fatty acids of the seed oil of *Microula sikkimensis* (1.2% [Wang Huiying, Yu Xuefian, Yi Yuanfen and Ding Jingkai Yunnan Zhiwu-Yajiu 1989, 11 (1), 60–4 (Ch.), L. Jing Jingmin, Wang Jingping, Yu Fenglan. Zhiwu Xuebao, 1989, 31 (1), 50–3 (Ch.) These reports do not mention isolation of the constituent and the content estimation based on GLC data.

*Indigofera tinctoria* has been in use in indigenous system of medicine in epilepsy, nervous disorders & bronchitis [Wealth of India, vol. 5. (Council of Scientific & Industrial Research, New Delhi) 182, (1959)]. The plant is also used as ointment in sores, old ulcers and haemorrhoids [R. N. Chopra, S. L. Nayar and I. C. Chopra, Glossary of Indian Medicinal Plants, 141 (1956)]. The leaves of the plants have been used in liver ailments [Nadkarni, K. M., Indian Materia Medica, vol. 1 (Popular Book Depot, Bombay, 680 (1954)]. Extract of the leaves of the plant has exhibited marked hepatoprotective effect against $CCl_4$ induced hepatic injury in rabbits, rats and mice at Regional Research Laboratory (RRL) Jammu. [Anand, K. K., Chand Dewan and Ghatak, B. J. Ray, Indian J. Exp. Biol., 17, 685 (1979); Anand, K. K., Chand Dewan, Ghatak, B. J. Ray and Arya, R. K., Indian J. Expl. Biol., 19, 298 (1981)].

Recent study in RRL Jammu for hepatoprotective effect of the plant extract and further bioactivity-guided fractionation has resulted in identification of trans-tetracos-15-enoic acid as the active principle. The constituent has been synthesized and observed to possess dose related hepatoprotective effect against galactosamine, paracetamol and $CCl_4$ as hepatotoxins using commercially available silymarin as reference material.

Activity of the formulation being described in the invention is not exactly equal to the sum of the activities of the two individual constituents and activity enhancement does not occur simply due to the mixing of the two compounds. This has been verified by mixing the formulation with RLJ-NE-299A, a standardized mixture of iridoid glycosides from *Picrorhiza kurroa* possessing hepatoprotective, immunostimulant and immunorestorative effects [Indian patent no. 178866].

The mixture of Apocynin, trans-tetracos-15-enoic acid prepared in many other proportions by weight have not shown any enhancement in hepatoprotective action and in some experiments the biological activity of the mixture is much less than the individual constituents.

OBJECTS OF THE INVENTION

The primary object of the invention is to provide a synergistic composition of trans-tetracos-15-enoic acid and Apocynin.

Another object of the present invention is to provide a method of treatment for hepatotoxicity.

Yet another object of the present invention is to provide a composition having broader spectrum of hepatoprotective activity than the established herbal product in use viz., Silymarin.

Still another object of the invention is to provide a composition having potential therapeutic application in obstructive and viral hepatitis.

SUMMARY OF THE INVENTION

The present invention relates to a synergistic hepatoprotective composition containing trans-tetracos-15-enoic acid (TCA) and Apocynin (APO). The present invention also relates to a method of treatment for hepatotoxicity in mammals and humans.

DETAILED DESCRIPTION OF THE INVENTION

Accordingly, the present invention provides a synergistic pharmaceutical composition having enhanced hepatoprotective activity on subjects, obtained from the plant *Indigofera tinctoria*, said composition comprising an effective amount of:

(a) trans-tetracos-15-enoic acid (TCA) obtained from the plant *Indigofera tinctoria*;
(b) Apocynin (APO) obtained from the plants *Apocyanum cannabium* and *A. androsaemifolium*; and
(c) the ratio of APO and TCA is in the range of 3:1 to 1:3.

An embodiment of the present invention, wherein the said composition is used either singly or in combination with pharmaceutically acceptable additives.

An another embodiment of the present invention, wherein the pharmaceutically acceptable additives are selected from the group consisting of carriers, diluents, solvents, filters lubricants, excipients, binder and stabilizers.

Yet another embodiment of the present invention, wherein the said composition is used for both preventive and curative properties.

Still another embodiment of the present invention, wherein the said composition is used systemically, orally or by any clinically/medically accepted methods.

Yet another embodiment of the present invention, wherein the said composition is used to treat hepatic disorders that are clinically, biochemically and histologically similar to that of viral hepatitis, chronic hepatitis, fatty liver, cirrhosis and several vascular lesions of the liver. Still another embodiment of the present invention, wherein the said composition is used to treat the liver damage induced by hepatotoxins.

Yet another embodiment of the present invention, wherein the hepatotoxins are selected from the group consisting of Galactosamine, Paracetamol and Carbon tetrachloride.

Still another embodiment of the present invention, wherein the subject is selected from the group consisting of mammals, humans and preferably humans.

Yet another embodiment of the present invention, wherein the dosage of said composition for the treatment of $CCl_4$ induced hepatotoxicity in mammals is 50 mg/kg-body weight.

Still another embodiment of the present invention, wherein said composition having the enhanced hepatoprotective activity in $CCl_4$ induced hepatotoxic mammals up to 92%.

Yet another embodiment of the present invention, wherein the dosage of said composition for the treatment of acetaminophen induced hepatotoxicity in mammals is 50 mg/kg-body weight. Still another embodiment of the present invention, wherein said composition having the enhanced hepatoprotective activity in acetaminophen induced hepatotoxicity in mammals up to 86%.

Yet another embodiment of the present invention, wherein said composition having the dosage of said composition for the treatment of Galactosamine induced hepatotoxicity in mammals 50 mg/kg of body weight.

Still another embodiment of the present invention, wherein said composition having the enhanced hepatoprotective activity in Galactosamine induced hepatotoxicity in mammals up to 75%.

Yet another embodiment of the present invention, the dosage of said composition for choretic activity in mammals to control bile flow and bile solids is 50 mg/kg of body weight. Still another embodiment of the present invention, wherein the enhanced choretic activity is up to 39%.

Yet another embodiment of the present invention, wherein the dosage of said composition for hepatic disorders in human beings is about 10 mg/kg of body weight.

The present invention also provides a method of treating subjects with liver disorders with an effective amount of synergistic pharmaceutical composition to induce enhanced hepatoprotective activity, said composition comprising:

(a) trans-tetracos-15-enoic acid (TCA) obtained from the plant *Indigofera tinctoria*;
(b) Apocynin (APO) obtained from the plants *Apocyanum cannabium* and *A. androsaemifolium*; and
(c) the ratio of APO and TCA is in the range of 3:1 to 1:3.

Still another embodiment of the present invention, wherein said method is used to treat liver disorders caused by Galactosamine, Paracetamol and Carbon tetrachloride.

Yet another embodiment of the present invention, a method wherein the dosage for the treatment of $CCl_4$ induced hepatotoxicity in mammals is about 50-mg/kg-body weight.

Still another embodiment of the present invention, a method wherein the enhanced hepatoprotective activity in $CCl_4$ induced hepatotoxic mammals is up to 92%.

Yet another embodiment of the present invention, a method wherein the dosage for the treatment of acetaminophen induced hepatotoxicity in mammals is 50 mg/kg-body weight.

Still another embodiment of the present invention, a method wherein the enhanced hepatoprotective activity in acetaminophen induced hepatotoxicity in mammals is up to 86%.

Yet another embodiment of the present invention, a method wherein the dosage for the treatment of Galactosamine induced hepatotoxicity in mammals is 50 mg/kg of body weight.

Still another embodiment of the present invention, a method wherein the enhanced hepatoprotective activity in Galactosamine induced hepatotoxicity in mammals is up to 75%.

Yet another embodiment of the present invention, a method wherein the dosage for choretic activity in mammals to control the bile flow and bile solids is 50 mg/kg of body weight.

Still another embodiment of the present invention, a method wherein the enhanced choretic activity in mammals is up to 39%.

Yet another embodiment of the present invention, a method wherein the composition is used either singly or in combination with pharmaceutically acceptable carriers.

Still another embodiment of the present invention, a method wherein the composition is administered to a subject in combination with pharmaceutically acceptable additives, carriers, diluents, solvents, filters, lubricants, excipients, binder or stabilizers.

Yet another embodiment of the present invention, a method wherein the desired dosage is administered for both preventive and curative properties.

Still another embodiment of the present invention, a method wherein the composition is administered systemically, orally or by any clinically/medically accepted methods.

Yet another embodiment of the present invention, a method wherein the subject is selected from animals, mammals, and preferably humans.

Still another embodiment of the present invention, a method wherein the preferred dosage for hepatic disorders in human beings is about 10–15 mg/kg of body weight.

The invention is further explained in the form of preferred embodiments.

i. Animals:

The pharmacological studies are conducted on Wistar albino rats (150–180 g) and Swiss albino mice (25–30 g) of either sex, colony—bred in the Institute's animal house. After procurement, all the animals are divided into different groups and are left for one week for acclimatization to experimentation room and are maintained on standard conditions (23±2° C., 60–70% relative humidity and 12 h photo period). The animals are fed with standard rodents pellet diet and water ad libitum. There are six animals in each group except for general behaviour and acute toxicity studies where ten animals are used in each group.

ii. Hepatotoxins:

It is emphasized that hepatotoxin that causes acute hepatitis should have close resemblance with the viral hepatitis, clinically, biochemically and histologically. Drugs are also causes of chronic hepatic disease as chronic hepatitis, fatty liver, cirrhosis and several vascular lesions of the liver. In many instances drug induced hepatitis proves indistinguishable from viral hepatitis. Chemically induced hepatic injury for experimental studies should be severe enough to cause cell death or to modify hepatic functions. The mechanism of acute hepatic injury depends upon the chemical compound and the species of animals used. Many chemicals produce parenchymal damage, arrest bile flow and cause jaundice (chloretic injury). Hepatoprotective activity against $CCl_4$, paracetamol and, D-galactosamine induced hepatotoxicity are studied.

Carbon Tetrachloride ($CCl_4$): $CCl_4$ is one of the most powerful hepatotoxins (in term of severity of injury). It causes toxic necrosis, which leads to biochemical changes having clinical features similar to those of acute viral hepatitis (Vogel, 1977, Bramanti et. al., 1978, Kumar et. al., 1992). Liver injury is produced by administration of $CCl_4$ mixed with liquid paraffin. Animals are given single dose of $CCl_4$ (50 $\mu l.kg^{-1}$, p.o.) in acute single treatment and (0.5 $ml.kg^{-1}$, p.o.) in case of multitreatment with drug. It is administered orally (p.o) by gastric intubation. The control animals received the equal volume of liquid paraffin. (Table 3, 4)

Paracetamol (APAP, Acetaminophen): It is a therapeutic agent widely used as analgesic/antipyretic drug. When taken in large doses it causes hepatic necrosis which leads to biochemical changes having clinical features similar to those of acute viral hepatitis in humans (Proudfoot and Wright, 1970). The similar effect is observed in animals. The toxic effect can be potentiated if it is given several hours after the anesthetic ether inhalation (Wells et. al., 1986).

Liver injury is induced by injecting paracetamol (200 $mg.kg^{-1}$) interaperitoneally in normal saline (pH 9.4) six hour after inhalation of anesthetic ether (4 ml/4 min/6 animals) in a closed chamber. The control animals received the equal volume of vehicle. (Table 2)

D-Galactosamine: It is one of the toxins that induce hepatic inflammatory conditions in the rat liver that clinically resembles to viral hepatitis. The mechanism of GalN induced liver injury has been extensively examined and this model is now accepted as one of the authentic systems of liver damage (Bauer et. al., 1974, A1-Tuwaijiri et. al., 1981). (Table 1)

Hepatic damage is produced by injecting GalN (300 $mg.kg^{-1}$) subcutaneously in normal saline. The control animals received the equal volume of vehicle.

iii. Treatment with Bio-Active Compound and Silymarin:

Freshly prepared suspension (1%, w/v) in 0.2% gum acacia in normal saline is used for all the experiments except for toxicity studies where (10%, w/v) suspension is used. Silymarin suspension (1%, w/v) in 0.2% gum acacia is used as a reference standard (positive control).

iv. Experimental Models:

Effect on Serum and Hepatic Biochemical Parameters:

$CCl_4$ Induced Hepatotoxicity:

Treatment of Test Material Before and After Hepatotoxin:
The doses of TCA and APO individually and in mixture, silymarin (50 mg/kg, p.o. each) and vehicle (normal saline) are fed to different groups of rats at 48 hours, 24 hours and 2 hours before and 6 hours after hepatotoxin ($CCl_4$, 0.5 $ml.kg^{-1}$, p.o.) intoxication. Blood is collected from orbital sinus in all the animals 18 hours after last treatment and serum separated for different estimations. All the animals are then killed by decapitation, their livers are quickly excised, cleaned of adhering tissue, weighed and homogenised in phosphate buffer saline for the analysis of hepatic parameters (Agarwal and Mehendale, 1983, Klingensmith and Mehendale, 1982, Zimmerman, 1973, Edmondson and Peter, 1985, Mitchell, et al, 1973). (Table 3–4).

Paracetamol Induced Hepatotoxicity:

Treatment of Test Material Before and After Hepatotoxin:
The doses of TCA and APO individually and in mixture, silymarin (50 mg/kg, p.o. each) and vehicle (normal saline) are fed to different groups of mice at 72 hours, 48 hours and 24 hours, 1 hour before diethyl ether inhalation and 1 hour after hepatotoxin (paracetamol, 200 $mg.kg^{-1}$, i.p.) given 6 hours after exposure to diethyl- ether. Blood is collected from orbital sinus in all the animals 18 hours after last treatment and serum separated for different estimations. A portion of the liver is processed for histopathological studies. (Table 2)

D-Galactosamine Induced Hepatotoxicity:

(a) Treatment of Test Material before and after Hepatotoxin:

The doses of TCA and APO individually and in mixture, silymarin (50 mg/kg, p.o. each) and vehicle (normal saline) are fed to different groups of mice at 48 hours, 24 hours and 2 hours before and 6 hours after hepatotoxin (GalN, 300 $mg.kg^{-1}$, s.c.) intoxication. Blood is collected from orbital sinus in all the animals 18 h after last treatment and serum separated for different estimations. All the animals are then killed by decapitation, their livers are quickly excised, cleaned of adhering tissue, weighed and homogenised in phosphate buffer saline for the analysis of hepatic parameters. A portion of the liver is processed for histopathological studies (Table 1)

Parameters Studied:

GPT and GOT: Pyruvate formed by transamination reaction is determined spectrophotometrically after reaction with 2,4-dinitrophenylhydrazine (Reitman and Frankel, 1957).

ALP: p-nitrophenol formed in alkaline medium is measured spectrophotometrically using p-nitrophenyl phosphate as substrate (Walter and Schutt, 1974).

Bilirubin : Total bilirubin is measured by diazotization reaction with $NaNO_2$ (Malloy and Evelyn, 1937)

Triglycerides: Triglycerides from serum are extracted with isopropanol and sopanified with KOH. The liberated glycerol is converted to formaldehyde by periodate and determined after reaction with acetyl acetone. Triolein is used as standard (Neri and Firings, 1973).

Glutathione: It is determined after deproteination by reaction with DTNB (Ellman 1959 as modified by David 1987).

Lipid peroxidation: Thiobarbituric acid reacting substances are determined spectrophotometrically at 535 nm. Buege. and Aust. (1978).

Hepatoprotective Activity:

Hepatoprotective activity (H) is calculated by the following equation:

$$H=[1-(TC-V/VC-V)]\times 100$$

Where TC, VC, and V are drug+toxin, vehicle+toxin and vehicle treated groups of animals respectively.

Human Dose:

Doses for human being can be calculated by equivalent surface area doses conversion factor (equivalency on the basis of mg/sq. m)

Effect on Bile Flow and Bile Solids

The liver, by producing bile, plays an important role in digestion. The presence of bile in the intestine is necessary to accomplish the digestion and absorption of fats as well as absorption of the fat-soluble vitamins—A, D, E & K. Bile is also an important vehicle of excretion. It removes many drugs, toxins, bile pigments and various inorganic substances either derived from the diet or synthesized by the body as cholesterol or as cholic acid. Increase in the bile flow is suggestive of stimulating action of liver microsomal enzymes.

Effect on the liver bile flow of test drug and that of vehicle is carried out after cannulating the bile duct in normal anaesthesied rats. Bile collected is from each animal from 0–5 hours (Klaassen, 1969, Donal et al. 1953). (Table 5)

Histopathological Studies:

Hitopathological studies: A portion of the liver after treatment of hepatotoxin (GalN, $CCl_4$, and paracetamol) and test material is processed for histopathological studies by routine hematoxyline and eosin stained sections (Krajian, A. A., 1963).

General Behaviour and Acute Toxicity:

Using different doses (10, 30, 100, 1200, 1400, 1600, 1800 and 2000 mg.$kg^{-1}$) of said composition given orally to the groups of 10 mice for each dose, while one group with same number of mice served as control. The animals are observed continuously for 1 hour and then half hourly for 4 hours for any gross behavioral changes and general motor activity, writhing, convulsion, response to tail pinching, gnawing, piloerection, pupil size, fecal output, feeding behaviour etc. and further up to 72 hours for any mortality. Acute $LD_{50}$ values in mice are calculated by the method of Miller and Tainter, (1944). Mortality of animals in all the groups used in different models for determining hepatoprotective activity during the period of treatment is also recorded as a rough index of subacute toxicity, Statistical Analysis.

The data obtained are subjected to statistical analysis using ANOVA for comparing different groups (Armitage, 1987) and Dunnett's t test for control and test groups (Dunnett, 1964). The regression coefficient (Slope b) correlation coefficient (r) with its p value and $ED_{50}$ with 95% confidence limit (CL) are determined by regression analysis using log dose and percent effect of adaptogenic activity (Swinscow, 1980). The two tailed paired student t test for comparing means before and after treatment and one tailed unpaired student t test for comparing control and drug treated groups (Ghosh, 1984) are used. The p value of <0.05 or less is taken as the criterion of significance.

TABLE 1

Hepatoprotective activity (in vivo) of TCA, APO, Mixture of TCA & APO (1:1) and silymarin (pre-treatment fed at 48 h, 24 h, 2 h before and 6 h after hepatotoxin) against the D-Galactosamine (GalN) [(300 mg $kg^{-1}$ in normal saline, subcutaneously (s.c.)] induced hepatic injury in rats[a]

| Treatment | Dose mg $kg^{-1}$ (p.o.) | Serum parameters | | | | | Hepatic parameters | |
|---|---|---|---|---|---|---|---|---|
| | | GPT (Units) | GOT (Units) | ALP[b] | Bilirubin (mg %) | Triglycerides (mg %) | Lipid peroxidation[c] | Glutathione[d] |
| Vehicle Control | — | 107.18 ± 13.48 | 112.65 ± 3.65 | 15.63 ± 2.02 | 0.13 ± 0.01 | 17.16 ± 2.07 | 28.33 ± 2.06 | 8.46 ± 0.77 |
| Vehicle + GalN | — | 1515.18 ± 68.09 | 756.78 ± 65.63 | 86.38 ± 5.68 | 0.61 ± 0.03 | 42.91 ± 2.19 | 62.26 ± 3.42 | 3.44 + 0.35 |
| TCA + GalN | 50 | 758.59 ± 40.86 (53.74) | 421.64 ± 30.36 (52.03) | 44.16 ± 2.87 (59.67) | 0.29 ± 0.03 (66.66) | 29.78 ± 2.82 (50.99) | 42.12 ± 3.93 (59.35) | 5.39 ± 0.43 (38.84) |
| APO + GalN | 50 | 859.18 ± 50.51 (46.59) | 509.33 ± 41.63 (38.42) | 37.73 ± 1.64 (68.76) | 0.41 ± 0.02 (41.66) | 31.85 ± 3.74 (42.95) | 48.71 ± 3.69 (39.93) | 4.52 ± 0.49 (21.51) |
| Mixture + GalN | 50 | 457.76 ± 19.48 (75.10) | 309.40 ± 26.52 (69.45) | 42.47 ± 2.14 (62.06) | 0.31 ± 0.01 (62.50) | 26.10 ± 3.28 (65.28) | 39.05 ± 3.37 (68.40) | 6.42 ± 0.40 (59.36) |
| Silymarin + GalN | 50 | 706.04 ± 55.79 (57.46) | 429.35 ± 46.94 (50.83) | 44.58 ± 3.34 (59.08) | 0.29 ± 0.02 (66.60) | 34.04 ± 3.41 (34.45) | 42.81 ± 2.52 (57.32) | 5.70 ± 0.42 (45.02) |

[a]Values represent the mean ± S.E. and within parentheses hepatoprotective activity percent of six animals in each group, Rats: Wistar, (150–175 g) male.
Unit: each unit is μmole pyruvate/min/L.
[b]is μmole of p-nitrophenol formed/min/L,
[c]is n moles MDA/g liver.,
[d]is μmole GSH/g liver

TABLE 2

Hepatoprotective activity (in vivo) of TCA, APO, Mixture of TCA & APO (1:1) and silymarin (Pre-treatment) fed at 72 h, 48 h, 24 h, 1 h before inhalation of diethyl-ether and 1 h after 'Acetaminophen' ((APAP) 200 mg $kg^{-1}$) given i.p. 6 h after exposure to diethyl-ether in mice[a]

| Treatment | Dose mg $kg^{-1}$ (p.o.) | Serum parameters | | | | | Hepatic parameters | |
|---|---|---|---|---|---|---|---|---|
| | | GPT (Units) | GOT (Units) | ALP[b] | Bilirubin (mg %) | Triglycerides (mg %) | Lipid Peroxidation[c] | Glutathione[d] |
| Vehicle Control | — | 137.15 ± 14.91 | 99.69 ± 11.02 | 18.46 ± 1.48 | 0.12 ± 0.01 | 15.47 ± 0.78 | 33.64 ± 2.53 | 6.85 ± 0.45 |
| Vehicle + PAP | — | 2210.46 ± 152.80 | 1124.89 ± 90.76 | 53.52 ± 2.98 | 0.66 ± 0.02 | 39.21 ± 2.22 | 57.45 ± 2.27 | 2.93 ± 0.33 |
| TCA + APAP | 50 | 1008.04 ± 63.66 (57.99) | 561.83 ± 51.52 (54.92) | 34.95 ± 1.89 (52.96) | 0.355 ± 0.01 (56.48) | 23.53 ± 1.77 (66.05) | 44.24 ± 2.22 (55.48) | 4.59 ± 0.45 (42.35) |
| APO + APAP | 50 | 1334.72 ± 98.34 (42.27) | 755.04 ± 112.04 (36.07) | 29.71 ± 1.89 (67.91) | 0.43 ± 0.01 (42.59) | 30.50 ± 1.36 (36.68) | 48.32 ± 2.13 (38.34) | 4.60 ± 0.42 (42.60) |
| Mixture + APAP | 50 | 747.36 ± 86.30 (70.57) | 409.27 ± 72.84 (69.80) | 23.25 ± 1.71 (86.33) | 0.388 ± 0.02 (50.37) | 23.62 ± 2.05 (65.67) | 44.12 ± 2.64 (55.98) | 4.31 ± 0.27 (35.20) |

TABLE 2-continued

Hepatoprotective activity (in vivo) of TCA, APO, Mixture of TCA & APO (1:1) and silymarin (Pre-treatment) fed at 72 h, 48 h, 24 h, 1 h before inhalation of diethyl-ether and 1 h after 'Acetaminophen' ((APAP) 200 mg kg$^{-1}$) given i.p. 6 h after exposure to diethyl-ether in mice[a]

| Treatment | Dose mg kg$^{-1}$ (p.o.) | Serum parameters | | | | | Hepatic parameters | |
|---|---|---|---|---|---|---|---|---|
| | | GPT (Units) | GOT (Units) | ALP[b] | Bilirubin (mg %) | Triglycerides (mg %) | Lipid Peroxidation[c] | Glutathione[d] |
| Silymarin + APAP | 50 | 1129.74 ± 62.49 (52.12) | 671.86 ± 69.00 (44.19) | 37.17 ± 1.35 (46.63) | 0.373 ± 0.02 (53.14) | 29.26 ± 1.79 (41.91) | 42.82 ± 2.22 (61.44) | 5.09 ± 0.22 (55.10) |

[a]Values represent the mean ± S.E. and within parentheses hepatoprotective activity percent of six animals in each group Mice: Swiss albino (25–30 g) male.
Unit: each unit is μmole pyruvate/min/L.
[b]is μmole of p-nitrophenol formed/min/L,
[c]is n moles MDA/g liver.,
[d]is μmole GSH/g liver

TABLE 3

Hepatoprotective activity (in vivo) of TCA, APO, Mixture of TCA & APO (1:1) and silymarin (pre-treatment fed at 48 h, 24 h, 2 h before and 6 h after hepatotoxin) against CCl$_4$ (0.5 ml kg$^{-1}$, p.o.) induced hepatic injury in rats[a]

| Treatment | Dose mg kg$^{-1}$ (p.o.) | Serum parameters | | | | | Hepatic parameters | |
|---|---|---|---|---|---|---|---|---|
| | | GPT (Units) | GOT (Units) | ALP[b] | Bilirubin (mg %) | Triglycerides (mg %) | Lipid peroxidation[c] | Glutathione[d] |
| Vehicle control | — | 118.18 ± 29.88 | 156.97 ± 27.97 | 23.44 ± 2.05 | 0.15 ± 0.02 | 15.47 ± 0.78 | 37.75 ± 2.74 | 6.96 ± 0.59 |
| Vehicle + CCl$_4$ | — | 931.00 ± 78.14 | 825.03 ± 68.95 | 52.42 ± 3.46 | 0.60 ± 0.03 | 39.21 ± 2.22 | 63.65 ± 3.80 | 3.54 ± 0.27 |
| TCA + CCl$_4$ | 50 | 324.84 ± 42.09 (74.63) | 409.73 ± 46.57 (62.16) | 28.72 ± 3.90 (81.78) | 0.35 ± 0.02 (55.55) | 23.53 ± 1.77 (66.05) | 46.88 ± 2.58 (64.33) | 5.35 ± 0.51 (52.92) |
| Mixture + CCl$_4$ | 50 | 448.74 ± 22.03 (59.33) | 472.09 ± 38.32 (52.83) | 25.75 ± 2.33 (92.03) | 0.30 ± 0.02 (66.66) | 23.62 ± 2.05 (65.67) | 49.58 ± 3.30 (53.79) | 50.50 ± 0.56 (44.15) |
| Silymarin + CCl$_4$ | 50 | 445.52 ± 43.48 (59.73) | 464.95 ± 32.39 (53.89) | 32.75 ± 2.54 (67.87) | 0.37 ± 0.02 (51.11) | 29.26 ± 1.79 (41.91) | 43.49 ± 2.07 (77.58) | 5.66 ± 0.29 (61.98) |

[a]Values represent the mean ± S.E. and within parentheses hepatoprotective activity percent of six animals in each group, Rats: Wistar, (150–175 g) male.
Unit: each unit is μmole pyruvate/min/L.,
[b]is μmole of p-nitrophenol formed/min/L,
[c]is n moles MDA/g liver.,
[d]is μmole GSH/g liver

TABLE 4

Hepatoprotective activity (in vivo) of TCA, APO, Mixture of TCA & APO (1:1) and silymarin (pre-treatment fed at 48 h, 24 h, 2 h before and 6 h after hepatotoxin) against CCl$_4$ (0.5 ml kg$^-$, p.o.) induced hepatic injury in rats[a]

| Treatment | Dose mg kg$^{-1}$ (p.o.) | Serum parameters | | | | | Hepatic parameters | |
|---|---|---|---|---|---|---|---|---|
| | | GPT (Units) | GOT (Units) | ALP[b] | Bilirubin (mg %) | Triglycerides (mg %) | Lipid peroxidation[c] | Glutathione[d] |
| Vehicle control | — | 87.88 ± 11.60 | 62.86 ± 13.16 | 21.92 ± 1.87 | 0.13 ± 0.02 | 10.69 ± 0.95 | 34.62 ± 2.69 | 6.55 ± 0.44 |
| Vehicle + CCl$_4$ | — | 1527.57 ± 76.47 | 765.64 ± 75.43 | 55.90 ± 2.43 | 0.60 ± 0.03 | 38.03 ± 1.65 | 58.21 ± 3.33 | 2.99 ± 0.41 |
| APO + CCl$_4$ | 50 | 838.58 ± 69.65 (47.86) | 489.39 ± 66.82 (39.31) | 26.66 ± 2.06 (86.05) | 0.37 ± 0.01 (48.94) | 28.00 ± 2.39 (36.68) | 48.12 ± 2.28 (42.77) | 4.44 ± 0.26 (40.73) |

[a]Values represent the mean ± S.E. and within parentheses hepatoprotective activity percent of six animals in each group, Rats: Wistar, (150–175 g) male.
Unit: each unit is μmole pyruvate/min/L.,
[b]is μmole of p-nitrophenol formed/min/L,
[c]is n moles MDA/g liver.,
[d]is μmole GSH/g liver

TABLE 5

Chloretic activity of TCA, APO, Mixture of TCA & APO (1:1) and Dehydrocholic acid (DHC) as percent increase in bile flow and bile solids when compared to normal values in rats[a].

| Treatment | Dose mg kg$^{-1}$ | Route | Bile parameters % Increase (as compared to normal) | |
|---|---|---|---|---|
| | | | Bile flow (ml %) | Bile solids (mg %) |
| TCA | 50 | i.d. | 08.23 ± 1.71 | 13.40 ± 1.53 |
| APO | 50 | i.d. | 27.39 ± 2.05 | 24.05 ± 2.76 |
| Mixture | 50 | i.d. | 39.46 ± 3.73 | 37.03 ± 4.15 |
| DHC | 50 | i.d. | 38.40 ± 2.76 | 28.13 ± 3.89 |

[a]Values represent mean ± SE of six animals in each group, Rats: Wistar 150–175 g) male
b: Values represent mean ± SE of eight animals in each group.

ADVANTAGES

Most of the hepatoprotective preparations/formulations available on the market are herbal based and hence are unstandardised chemically as well as biologically. Efficacy of the herbal formulations are known to be dependent upon secondary metabolites and reliability of these can only be assured if batch to batch standardization (chemical and pharmacological) are carried out.

In the present invention
 a). Chemical composition of the formulation is well described, hence reproducible biological activity is assured.
 b). Activity parameters are of broader spectrum and hence effectiveness of the formulation in obstructive and viral hepatitis.
 c). Pharmacological evaluation data of the formulation clearly indicates synergistic action of the constituents of the formulation.

What is claimed is:

1. A pharmaceutical composition having hepatoprotective activity on subjects, said composition comprising an effective amount of:
 (a) trans-tetracos-15-enoic acid (TCA) obtained from the plant *Indigofera tinctoria;*
 (b) Apocynin (APO) obtained from the plains *Apocyanum cannabium* and *A. androsaemifolium*; and
 the ratio of APO and TCA is in the range of 3:1 to 1:3.

2. A composition according to claim 1 wherein said composition is used either singly or in combination with pharmaceutically acceptable additives.

3. A composition according to claim 1 wherein the pharmaceutically acceptable additives are selected front the group consisting of carriers, diluents, solvents, filters lubricants, excipient, binder and stabilizers.

4. A composition according to claim 1 wherein the said composition is used for both preventive and curative properties.

5. A composition according to claim 1 wherein said composition is administered systemically, orally or by any clinically/medically accepted methods.

6. A composition according to claim 1 wherein the composition is used to treat hepatic disorders that are clinically, biochemically and histologically similar to that of viral hepatitis, chronic hepatitis, fatty liver, and several vascular lesions of the liver.

7. A composition according to claim 1 wherein said composition is used to treat the liver damage induced by hepatotoxins.

8. A composition according to claim 1 wherein the hepatotoxins are selected from the group consisting of Galactosamine, Paracetamol and Carbon tetrachloride.

9. A composition according to claim 1, wherein the subject is a mammal.

10. A composition according to claim 1 wherein the composition is characterized by hepatoprotective activity in a mammalian subject suffering from $CCl_4$-induced hepatotoxicity at a dosage of 50 mg/kg-body weight.

11. A composition according to claim 1 wherein the composition is characterized by up to 92% hepatoprotective activity in a mammalian subject suffering from $CCl_4$-induced hepatotoxicity.

12. A composition according to claim 1 wherein the composition is characterized by hepatoprotective activity in a mammalian subject suffering from acetaminophen-induced hepatotoxicity at a dosage of 50 mg/kg-body weight.

13. A composition according to claim 1 wherein the composition is characterized by up to 86% hepatoprotective activity in a mammalian subject suffering from acetaminophen-induced hepatotoxicity.

14. A composition according to claim 1 wherein the composition is characterized by hepatoprotective activity in a mammalian subject suffering from Galactosamine-induced hepatotoxicity at a dosage of 50 mg/kg-body weight.

15. A composition according to claim 1 wherein the composition is characterized by up to 75% hepatoprotective activity in a mammalian subject suffering from Galactosamine-induced hepatotoxicity.

16. A composition according to claim 1 wherein die composition a characterized by chloretic activity in a mammalian subject to control bile flow and bile solids at a dosage of 50 mg/kg of body weight.

17. A composition according to claim 1 wherein the composition is characterized by up to 39% chloretic activity in a mammalian subject.

18. A composition according to claim 1 wherein the composition is characterized by efficacy in a human subject suffering from hepatic disorders at a dosage of about 10–15 mg/kg of body weight.

19. A method of treating subjects with liver disorders with an effective amount of synergistic pharmaceutical composition to induce enhanced hepatoprotective activity, said composition comprising:
 (a) trans-tetracos 15-enoic acid (TCA) obtained from the plant *Indigofera tinctoria*;
 (b) Apocynin (APO) obtained from the plants *Apocyanum cannabium* and *A. androsaemifolium*; and
 (c) the ratio of APO and TCA is in the range of 3:1 to 1:3.

20. A method according to claim 19 wherein said composition is used to treat liver disorders caused by Galactosamine, Paracetamol and Carbon tetrachloride.

21. A method according to claim 19 wherein the dosage for the treatment of $CCl_4$ induced hepatotoxicity in mammals is about 50mg/kg-body weight.

22. A method according to claim 19 wherein the enhanced hepatoprotective activity in CCl4 induced hepatotoxic mammals is upto 92%.

23. A method according to claim 19 wherein the dosage for the treatment of acetaminophen induced hepatotoxicity in mammals is 50 mg/kg-body weight.

24. A method according to claim 19 wherein the enhanced hepatoprotective activity in acetaminophen induced hepatotoxicity in mammals is up to 86%.

25. A method according to claim 19 wherein the dosage for the treatment of Galactosamine induced hepatotoxicity in mammals is 50 mg/kg of body weight.

26. A method according to claim 19 wherein the enhanced hepatoprotective activity in Galactosamine induced hepatotoxicity in mammals is upto 75%.

27. A method according to claim 19 wherein the dosage for chloretic activity in mammals to control the bile flow and bile solids is 50mg/kg of body weight.

28. A method according to claim 19 wherein the composition is administered to a subject in combination with pharmaceutically acceptable additives, carriers, diluents. solvents, filters, lubricants, excipients, binder or stabilizers.

29. A method according to claim 19 wherein the desired dosage is administered for both preventive and curative properties.

30. A method according to claim 19 wherein said composition is administered systemically, orally or by any clinically/medically accepted methods.

31. A method according to claim 19 wherein the preferred dosage for hepatic disorders in human beings is about 10-15mg/kg of body weight.

32. A method according to claim 19 wherein the enhanced cholretic activity in mammals is up to 39%.

33. A method according to claim 19 wherein the composition is used either singly or in combination with pharmaceutically acceptable carriers.

34. A method according to claim 19 wherein the subject is a mammal.

35. A method according to claim 19 wherein the subject is a human.

36. A composition according to claim 9 wherein the subject is a human.

* * * * *

UNITED STATES PATENT AND TRADEMARK OFFICE
CERTIFICATE OF CORRECTION

PATENT NO. : 6,949,586 B2 Page 1 of 1
APPLICATION NO. : 10/102147
DATED : September 27, 2005
INVENTOR(S) : Sukhdev Swami Handa et al.

It is certified that error appears in the above-identified patent and that said Letters Patent is hereby corrected as shown below:

TITLE page, (73) Assignee: "Council of Scientific Research (IN)" should be
-- COUNCIL OF SCIENTIFIC AND INDUSTRIAL RESEARCH (IN) --.

Column 11, line 51, "front" should be -- from --.

Column 11, line 63, after "fatty liver", insert -- cirrhosis --.

Column 12, lines 30 and 31, "die" should be -- the -- and "a" should be -- is --.

Column 14, Line 45, "tetracos 15, should be -- tetracos-15 --.

Column 12, line 55, "50mg/kg" should be -- 50-kg/mg --.

Column 12, line 57, "CC14" should be -- $CCl_4$ --.

Column 12, line 58, "upto" should be -- up to --.

Signed and Sealed this

Nineteenth Day of September, 2006

JON W. DUDAS
*Director of the United States Patent and Trademark Office*